United States Patent
Belohlavek et al.

(10) Patent No.: US 6,533,728 B1
(45) Date of Patent: Mar. 18, 2003

(54) METHOD AND APPARATUS FOR RECOVERY AND PARAMETRIC DISPLAY OF CONTRAST AGENTS IN ULTRASOUND IMAGING

(75) Inventors: Marek Belohlavek, Rochester, MN (US); Richard Y. Bae, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/989,627

(22) Filed: Nov. 20, 2001

(51) Int. Cl.⁷ .................................................. A61B 8/14
(52) U.S. Cl. ...................................................... 600/458
(58) Field of Search ................................ 600/437, 441, 600/442, 443, 447, 454, 455, 458; 73/625, 626; 367/7, 11

(56) References Cited

U.S. PATENT DOCUMENTS

| 5,255,683 | A | 10/1993 | Monaghan |
|---|---|---|---|
| 5,526,816 | A | 6/1996 | Arditi |
| 5,833,613 | A | 11/1998 | Averkiou et al. |
| 5,961,464 | A | 10/1999 | Poland |
| 6,080,107 | A | 6/2000 | Poland |
| 6,186,951 | B1 | 2/2001 | Lizzi et al. |
| 6,458,083 | B1 * | 10/2002 | Jago et al. .................. 600/443 |

* cited by examiner

Primary Examiner—Marvin M. Lateef
Assistant Examiner—Ali M. Imam
(74) Attorney, Agent, or Firm—Quarles & Brady LLP

(57) ABSTRACT

A method for detecting the presence of contrast agent in the body of the patient initially transmits ultrasound pulses along respective acoustic scan lines, which pulses exhibit a fundamental transmission frequency. A set of returned signals are received along a respective scan line after each pulse transmission. The return signals are mathematically reconstructed to provide a first spectral component around the fundamental frequency and a second spectral component around a harmonic frequency. The peak amplitude of the reconstructed spectral components are compared to determine whether a contrast agent is present in the tissue, and hence to differentiate myocardium and perfused myocardium.

21 Claims, 7 Drawing Sheets

DISPLAY SYSTEM

METHOD AND APPARATUS FOR RECOVERY AND PARAMETRIC DISPLAY OF CONTRAST AGENTS IN ULTRASOUND IMAGING

TECHNICAL FIELD

The present invention relates to improved methods and apparatus for use of a contrast agent in ultrasonic imaging and, in particular, to improved methods and apparatus for the detection and measurement of contrast agents in regions of interest.

BACKGROUND ART

Ultrasonic transducers and imaging systems are used in many medical applications and, in particular, for the non-invasive acquisition of images of organs and conditions within a patient, typical examples being the ultrasound imaging of fetuses and the heart. Such systems commonly use a linear or phased array transducer having multiple transmitting and receiving elements to transmit and receive narrowly focused and "steerable" beams, or "lines", of ultrasonic energy into and from the body. The received beams, or lines, are reflected from the body's internal structures and contain amplitude or phase information, or both, that is used to generate images of the body's internal structures.

A primary problem in ultrasonic imaging has been that many of the body's internal structures have similar characteristics as regards the reflection of ultrasonic energy, so that it is difficult to obtain as clear and detailed images of many of the structures as is desired. In particular, many of the structures of interest, such as the muscles of the heart, are perfused with blood, so that it is difficult to distinguish between blood vessels and the chambers of the heart and the heart muscles.

This problem led to the development of alternative methods for imaging certain of the body's structures, such as the blood vessels of the heart. One of the most common imaging techniques, for example, is referred to as an angiogram and requires the injection of a radiofluorescent dye into the vessels to image the blood vessels of the heart with x-rays. Such techniques, however, are invasive or are otherwise unsatisfactory. For example, the use of x-ray imaging carries the risk of potential injury from radiation and involves complex, expensive and hazardous equipment. Also, radiofluorescent dyes are potentially toxic to at least some patients and are not broken down in the body but are flushed from the body by natural waste processes, often requiring hours to disappear from the body.

A more recent development has been ultrasonic imaging using contrast agents injected into the blood stream. Ultrasonic contrast agents are now commercially available and are essentially small bubbles of gas, such as air, formed by agitating a liquid or bubbling gas through a liquid, such as a saline solution or a solution containing a bubble forming compound, such as albumin. When insonicated, the bubbles resonate at their resonant frequency and emit energy at both the fundamental and second harmonic of their resonant frequency, thereby returning an enhanced signal at or around these frequencies and thereby providing an enhanced image of the liquid or tissue containing the contrast agent. It is also well known that the bubbles "disappear" when insonicated and the current theory is that the insonication ruptures the bubble's shell, thereby allowing the gas to dissipate into the surrounding liquid or tissue.

The use of ultrasonic contrast agents is thereby advantageous in allowing enhanced imaging using ultrasonics rather than x-rays, thereby eliminating the radiation hazard and allowing the use of equipment that is significantly less expensive and hazardous to use. Also, the agents are non-toxic and dissolve relatively quickly into waste products, such as air and albumin, that are normally found in the body and that are themselves non-toxic. Further, the insonication of the agent in itself destroys the agent, so that the agent can effectively be "erased" during the imaging process to a degree.

There are, however, a number of persistent problems in ultrasonic imaging using contrast agents. Conventional harmonic ultrasound methods for perfusion analysis require an initial set of data to be acquired before a contrast agent is injected, and a second set of data to be acquired after the contrast agent is injected. Therefore, a number of scans are required, and a significant amount of clinical time is needed to collect data. Furthermore, after the data is obtained, it can be difficult to correlate a region of interest in successive sets of data.

An alternative method for perfusion analysis in ultrasonic contrast agent imaging is harmonic imaging. Harmonic imaging is based on the strong harmonics produced when the "bubbles" of a contrast agent respond to transmitted ultrasound in a non-linear fashion. The reflected signals are processed using filters which provide a first spectrum around a fundamental frequency and a second spectrum around a harmonic frequency. Characteristics of the harmonic and fundamental spectra are compared to determine the comparative amount of signal due to tissue and the amount of signal due to contrast agent. The filters are generally bandpass filters centered around a first frequency, at the fundamental frequency, and a second frequency centered at the expected location of the second harmonic frequency. While useful in some applications, however, there are also problems associated with this type of harmonic imaging. Most importantly, the filtering method used to process the signals expects the second harmonic being located in a predetermined location. In most clinical situations, however, the center frequency of harmonic spectra is displaced by attenuation. Therefore, the results of the harmonic imaging can be inconsistent, or even inaccurate, particularly when the signal is attenuated. Furthermore, the bandpass filter does not filter noise or spurious signals which vary the amplitude of the signal. Since the amplitude at the center of the fundamental frequency and the second harmonic are frequently in calculations for locating the contrast agent and characterizing the tissue, the results are prone to inaccuracies.

The present invention provides a solution to these and other problems of the prior art by providing improved methods for the use of contrast agents in conjunction with ultrasound imagery, and in particular for identifying a contrast agent and characterizing the associated tissue.

SUMMARY OF THE INVENTION

The present invention is a method and apparatus for contrast perfusion data recovery using ultrasound signals. A contrast agent comprising microbubbles is injected into a subject. An ultrasound pulse signal exhibiting a characteristic frequency is directed at a region of interest in the subject, and a corresponding reflected signal is received by the transceiver. Using mathematical synthesizing or reconstruction techniques, a first spectrum is reconstructed from the broadband spectrum around the characteristic or fundamental transmission frequency, and a second, harmonic spectrum is reconstructed from the broadband spectrum around a harmonic frequency. Thereafter, a relationship is determined between the energy characteristics at the fundamental frequency and at the harmonic frequency. The determined relationship indicates a proportion of the return signal that is returned from contrast agent versus a proportion which is returned from tissue, and can therefore be used to characterize the tissue, and more particularly, to identify myocardial perfusion.

In a preferred embodiment of the invention least square error fitting procedures are employed to synthesize the Fourier broadband spectrum. To reconstruct the fundamental spectrum, a constrained Gaussian curve and least squares error fitting procedure are employed. Initially, a broadband harmonic spectrum is produced from the received signal. Next, a Gaussian curve is selected to have a center frequency substantially equivalent to the expected center frequency of the fundamental spectrum. The reconstructed fundamental spectrum is then subtracted from the received broadband spectrum to produce a spectrum mainly comprising the harmonic component. The harmonic spectrum is then reconstructed, again using a least square technique to reconstruct a Gaussian signal. Here, however, the center frequency and standard deviation are not predetermined, although limits on the spectral values are imposed to avoid the fundamental range and to maintain the signals within the effective range of the transceiver. Since the harmonic spectrum is not constrained to a center frequency, the resultant reconstructed harmonic spectrum can more accurately reflect the actual harmonic spectrum, and can account for attenuation in the signal.

In contrast to prior art techniques which employ filtering or other processes to extract the fundamental and harmonic components, the present invention therefore mathematically synthesizes or reconstructs the fundamental and harmonic components. This process results in a more accurate representation of the reflected signal, and therefore provides a more accurate characterization of the relative level of contrast agent in the tissue, as well as a more accurate characterization of the tissue.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
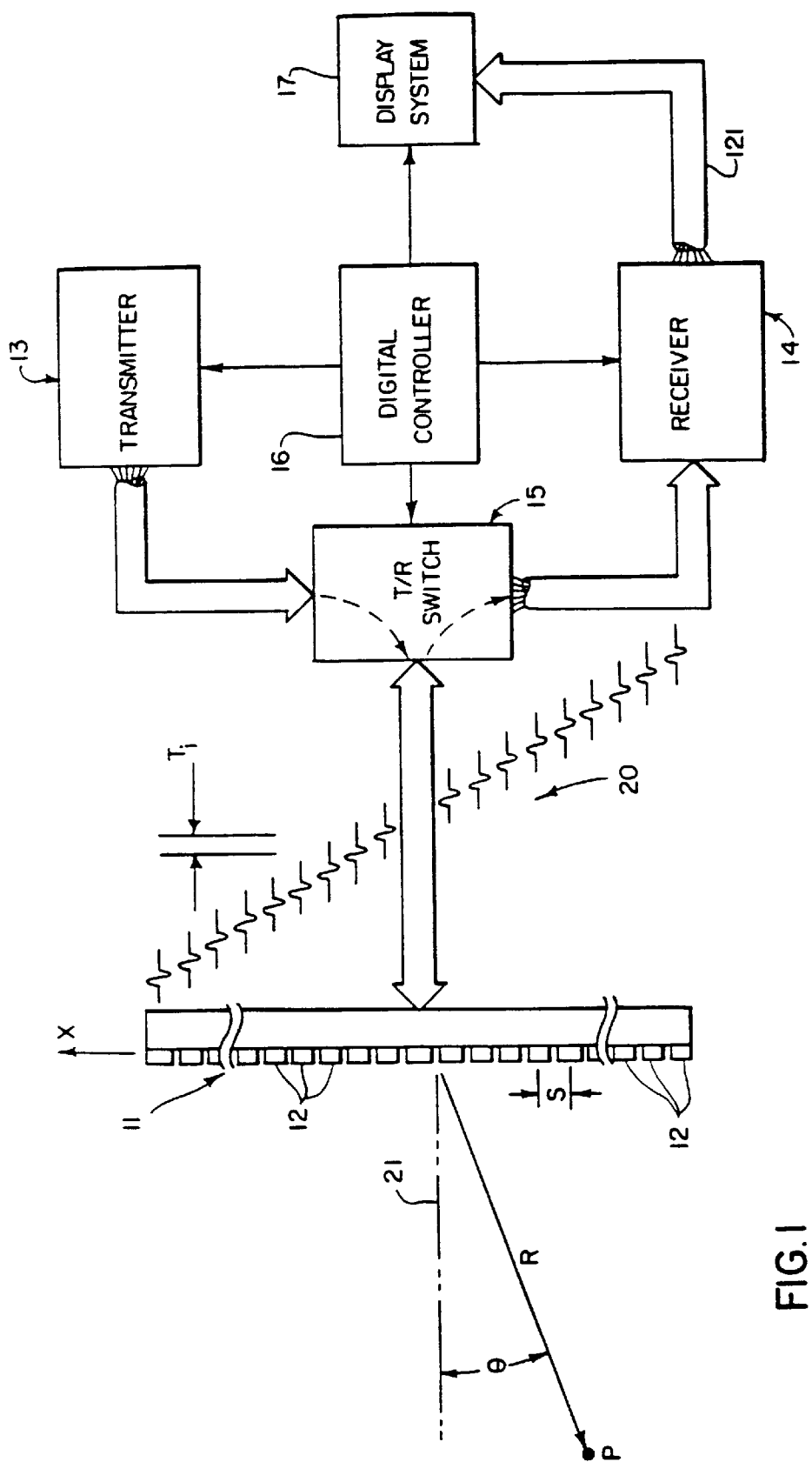
FIG. 1 is a block diagram of an ultrasonic imaging system which employs the present invention.

Referring particularly to FIG. 1, an ultrasonic imaging system includes a transducer array 11 comprised of a plurality of separately driven elements 12 which each produce a burst of ultrasonic energy when energized by a pulse produced by a transmitter 13. The ultrasonic energy reflected back to the transducer array 11 from the subject under study is converted to an electrical signal by each transducer element 12 and applied separately to a receiver 14 through a set of switches 15. The transmitter 13, receiver 14 and the switches 15 are operated under the control of a digital controller 16 responsive to the commands input by the human operator. A complete scan is performed by acquiring a series of echoes in which the switches 15 are set to their transmit position, the transmitter 13 is gated on momentarily to energize each transducer element 12, the switches 15 are then set to their receive position, and the subsequent echo signals produced by each transducer element 12 are applied to the receiver 14. The separate echo signals from each transducer element 12 are combined in the receiver 14 to produce a single echo signal which is employed to produce a line in an image on a display system 17.

The transmitter 13 drives the transducer array 11 such that the ultrasonic energy produced is directed, or steered, in a beam. A B-scan can therefore be performed by moving this beam through a set of angles from point-to-point rather than physically moving the transducer array 11. To accomplish this the transmitter 13 imparts a time delay (Ti) to the respective pulses 20 that are applied to successive transducer elements 12. If the time delay is zero (Ti=0), all the transducer elements 12 are energized simultaneously and the resulting ultrasonic beam is directed along an axis 21 normal to the transducer face and originating from the center of the transducer array 11. As the time delay (Ti) is increased as illustrated in FIG. 1, the ultrasonic beam is directed downward from the central axis 21 by an angle θ. The relationship between the time delay increment Ti added successively to each ith signal from one end of the transducer array (i=1) to the other end (i=n) is given by the following relationship:

$$Ti=(i-(n-1)/2)d \sin \theta/c+(i-(n-1)/2)2d2 \cos 2\theta/2RTc+To \qquad (1)$$

where d=equal spacing between centers of adjacent transducer elements 12, c=the velocity of sound in the object under study.

RT=range at which transmit beam is to be focused.

To=delay offset which insures that all calculated values (Ti) are positive values.

The first term in this expression steers the beam in the desired angle θ, and the second is employed when the transmitted beam is to be focused at a fixed range. A sector scan is performed by progressively changing the time delays Ti in successive excitations. The angle θ is thus changed in increments to steer the transmitted beam in a succession of directions. When the direction of the beam is above the central axis 21, the timing of the pulses 20 is reversed, but the formula of equation (1) still applies.

Referring still to FIG. 1, the echo signals produced by each burst of ultrasonic energy emanate from reflecting objects located at successive positions (R) along the ultrasonic beam. These are sensed separately by each segment 12 of the transducer array 11 and a sample of the magnitude of the echo signal at a particular point in time represents the amount of reflection occurring at a specific range (R). Due to the differences in the propagation paths between a focal point P and each transducer element 12, however, these echo signals will not occur simultaneously and their amplitudes will not be equal. The function of the receiver 14 is to amplify and demodulate these separate echo signals, impart the proper time delay to each and sum them together to provide a single echo signal which accurately indicates the total ultrasonic energy reflected from each focal point P located at range R along the ultrasonic beam oriented at the angle θ.

To simultaneously sum the electrical signals produced by the echoes from each transducer element 12, time delays are introduced into each separate transducer element channel of the receiver 14. In the case of the linear array 11, the delay introduced in each channel may be divided into two components, one component is referred to as a beam steering time delay, and the other component is referred to as a beam focusing time delay. The beam steering and beam focusing time delays for reception are precisely the same delays (Ti) as the transmission delays described above. However, the focusing time delay component introduced into each receiver channel is continuously changing during reception of the echo to provide dynamic focusing of the received beam at the range R from which the echo signal emanates. This dynamic focusing delay component is as follows:

$$Tk = (k-(n-1)/2)2d2 \cos 2\theta/2Rc \quad (2)$$

R=the range of the focal point P from the center of the array 11;

c=the velocity of sound in the object under study; and

Tk=the desired time delay associated with the echo signal from the kth element to coherently sum it with the other echo signals.

Under the direction of the digital controller 16, the receiver 14 provides delays during the scan such that the steering of the receiver 14 tracks with the direction of the beam steered by the transmitter 13 and it samples the echo signals at a succession of ranges and provides the proper delays to dynamically focus at points P along the beam. Thus, each emission of an ultrasonic pulse results in the acquisition of a series of data points which represent the amount of reflected sound from a corresponding series of points P located along the ultrasonic beam.

The display system 17 receives the series of data points produced by the receiver 14 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles (θ) is performed to provide the data necessary for display.

Figure 2:
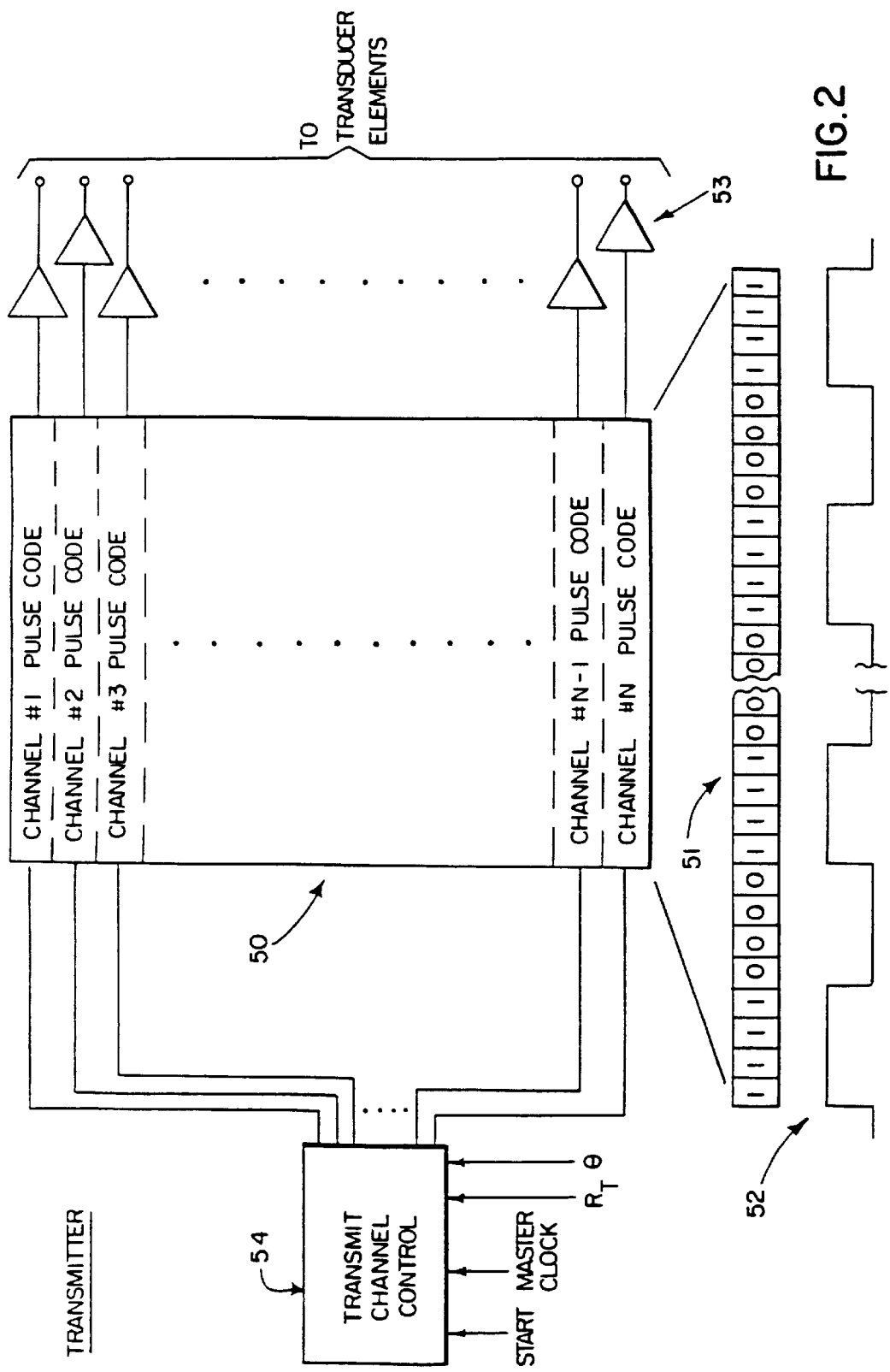
FIG. 2 is a block diagram of a transmitter which forms part of the system of FIG. 1.

Referring particularly to FIG. 2, the transmitter 13 includes a set of channel pulse code memories which are indicated collectively at 50. In the preferred embodiment there are 64 separate transducer elements 12, and therefore, there are 64 separate channel pulse code memories 50. Each pulse code memory 50 is typically a 1-bit by 512-bit memory which stores a bit pattern 51 that determines the frequency of the ultrasonic pulse 52 that is to be produced. In the preferred embodiment this bit pattern is read out of each pulse code memory 50 by a 40 MHz master clock and applied to a driver 53 which amplifies the signal to a power level suitable for driving the transducer 11. In the example shown in FIG. 2, the bit pattern is a sequence of four "1" bits alternated with four "0" bits to produce a 5 MHz ultrasonic pulse 52. The transducer elements 11 to which these ultrasonic pulses 52 are applied respond by producing ultrasonic energy. If all 512 bits are used, a pulse of bandwidth as narrow as 40 kHz centered on the carrier frequency (i.e. 5 MHz in the example) will be emitted.

As indicated above, to steer the transmitted beam of the ultrasonic energy in the desired direction (θ), the pulses 52 for each of the N channels must be delayed by the proper amount. These delays are provided by a transmit control 54 which receives four control signals (START, MASTER CLOCK, RT and θ) from the digital controller 16 (FIG. 1). Using the input control signal θ, the fixed transmit focus RT and the above equation (1), the transmit control 54 calculates the delay increment Ti required between successive transmit channels. When the START control signal is received, the transmit control 54 gates one of four possible phases of the 40 MHz MASTER CLOCK signal through to the first transmit channel 50. At each successive delay time interval (Ti) thereafter, the 40 MHz MASTER CLOCK signal is gated through to the next channel pulse code memory 50 until all N=128 channels are producing their ultrasonic pulses 52. Each transmit channel 50 is reset after its entire bit pattern 51 has been transmitted and the transmitter 13 then waits for the next θ and next START control signals from the digital controller 16. As indicated above, in the preferred embodiment of the invention a complete B-scan is comprised of 128 ultrasonic pulses steered in Δθ increments of 0.70° through a 90° sector centered about the central axis 21 (FIG. 1) of the transducer 11.

For a detailed description of the transmitter 13, reference is made to U.S. Pat. No. 5,014,712 issued on May 14, 1991 and entitled "Coded Excitation For Transmission Dynamic Focusing of Vibratory Energy Beam", incorporated herein by reference.

Figure 3:
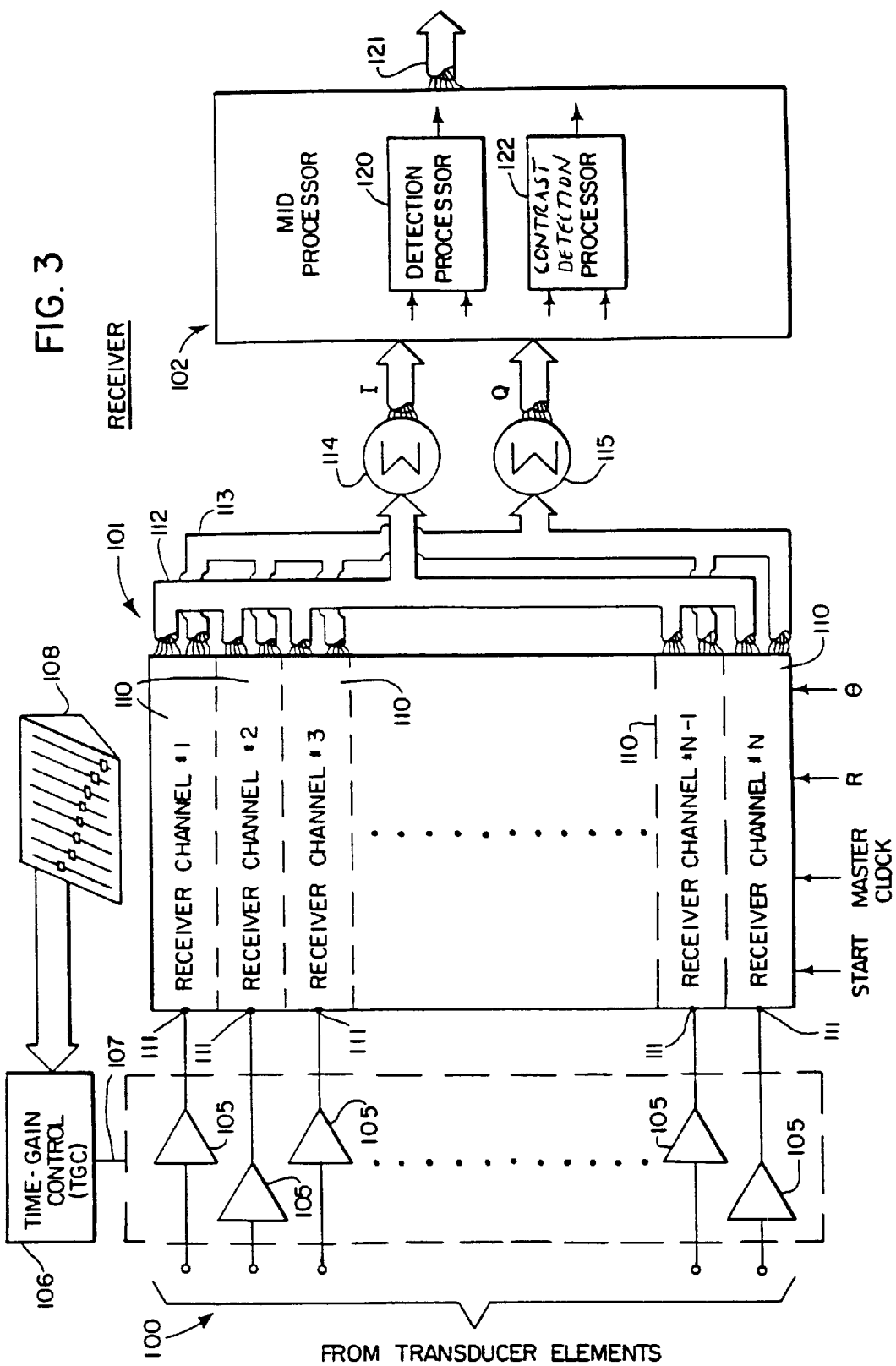
FIG. 3 is a block diagram of a receiver which forms part of the system of FIG. 1.

Referring particularly to FIG. 3, the receiver 14 is comprised of three sections: a time-gain control section 100, a beam forming section 101, and a mid processor 102. The time-gain control section 100 includes an amplifier 105 for each of the N=128 receiver channels and a time-gain control circuit 106. The input of each amplifier 105 is connected to a respective one of the transducer elements 12 to receive and amplify the echo signal which it receives. The amount of amplification provided by the amplifiers 105 is controlled through a control line 107 that is driven by the time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets eight (typically) TGC linear potentiometers 108 to values which provide a relatively uniform brightness over the entire range of the sector scan. The time interval over which the echo signal is acquired determines the range from which it emanates, and this time interval is divided into eight segments by the TGC control circuit 106. The settings of the eight potentiometers are employed to set the gain of the amplifiers 105 during each of the eight respective time intervals so that the echo signal is amplified in ever increasing amounts over the acquisition time interval.

The beam forming section 101 of the receiver 14 includes N=128 separate receiver channels 110. As will be explained in more detail below, each receiver channel 110 receives the analog echo signal from one of the TGC amplifiers 105 at an input 111, and it produces a stream of digitized output values on an I bus 112 and a Q bus 113. Each of these I and Q values represents a sample of the echo signal envelope at a specific range (R). These samples have been delayed in the manner described above such that when they are summed at summing points 114 and 115 with the I and Q samples from each of the other receiver channels 110, they indicate the magnitude and phase of the echo signal reflected from a point P located at range R on the steered beam (θ). In the preferred embodiment, each echo signal is sampled at intervals of about 150 micrometers over the entire range of the scan line (typically 40 to 200 millimeters).

For a more detailed description of the receiver 14, reference is made to U.S. Pat. No. 4,983,970 which issued on Jan. 8, 1991 as is entitled "Method And Apparatus for Digital Phase Array Imaging", and which is incorporated herein by reference.

Referring still to FIG. 3, the mid processor section 102 receives the beam samples from the summing points 114 and 115. The I and Q values of each beam sample is a 16-bit digital number which represents the in-phase and quadrature components of the magnitude of the reflected sound from a point (R,θ). The mid processor 102 can perform a variety of calculations on these beam samples, where choice is determined by the type of image to be reconstructed.

In accordance with the present invention, the mid processor 102 is programmed to image the relative presence of a contrast agent in tissue in a region of interest. Prior to imaging, a subject is injected with a contrast agent comprising microbubbles filled a relatively non-diffusible molecular weight gas. Examples of suitable contrast agents include Optison produced by Mallinckodt, Inc. of St. Louis, Miss., and Sonazid produced by Amersham PLC, of Buckinghamshire, UK. When the ultrasound pulsed wave strikes the microbubble, the ultrasound pulse wave is reflected at the interface of the bubble surface and the surrounding fluid, and pulses at its characteristic or resonant frequency. The bubbles, therefore, become a source of sound which contain characteristic fundamental and harmonic spectra.

To identify tissue carrying the contrast agent in accordance with the present invention, the mid-processor 102 employs a contrast detection processor 122 which receives the I and Q values and processes the data to provide a characterization of the data based on a mathematical relationship between the fundamental and harmonic components of the reflected or echo signal. The mathematical relationship can comprise a difference between the peak amplitude at the fundamental and harmonic components, or a ratio such as an harmonic to fundamental ratio ($HFR_p$) parameter. The mathematic characterization provides an indication of the degree to which a contrast agent is present in the tissue, and can therefore be used to characterize the tissue. More specifically, these parameters can be used to evaluate myocardial perfusion, as described below.

Figure 5:
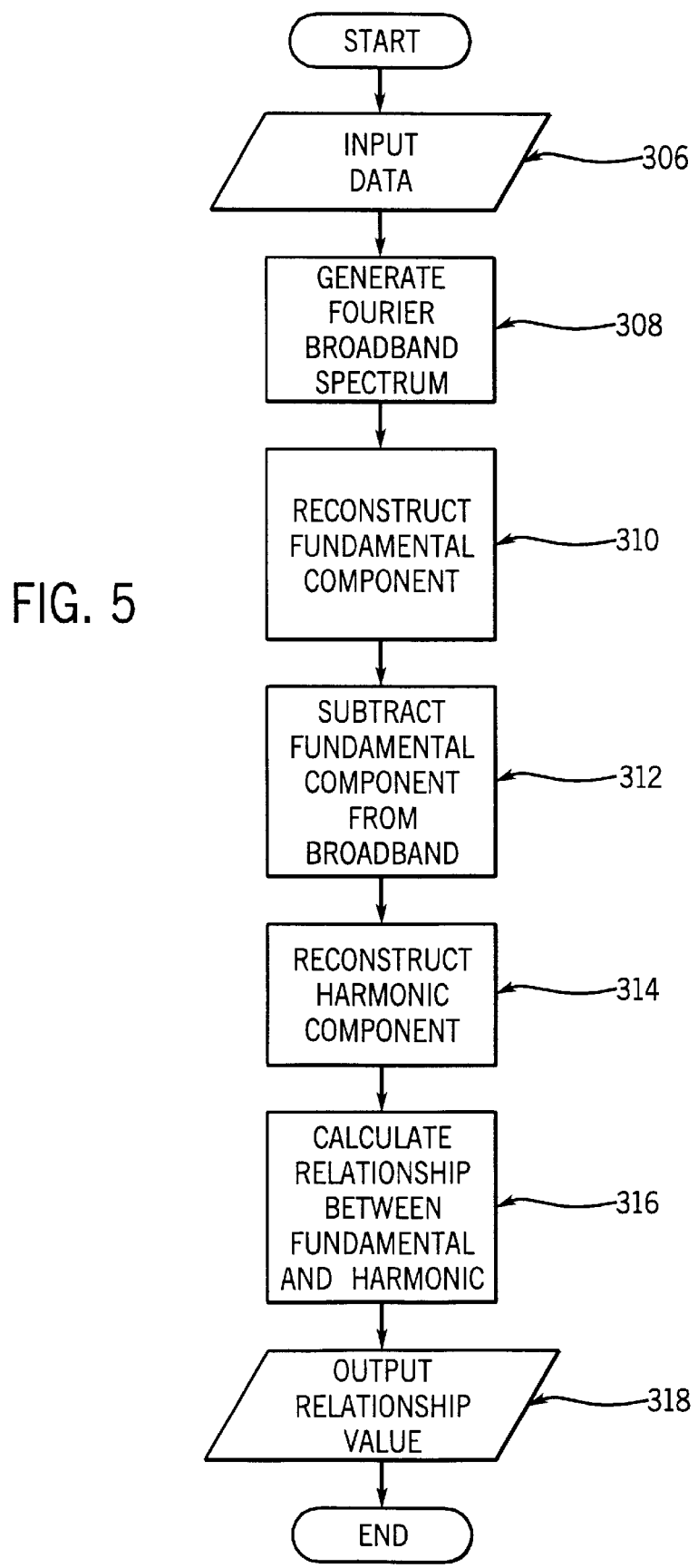
FIG. 5 is a flow chart illustrating the process steps of a preferred embodiment of the invention.
Figure 6:
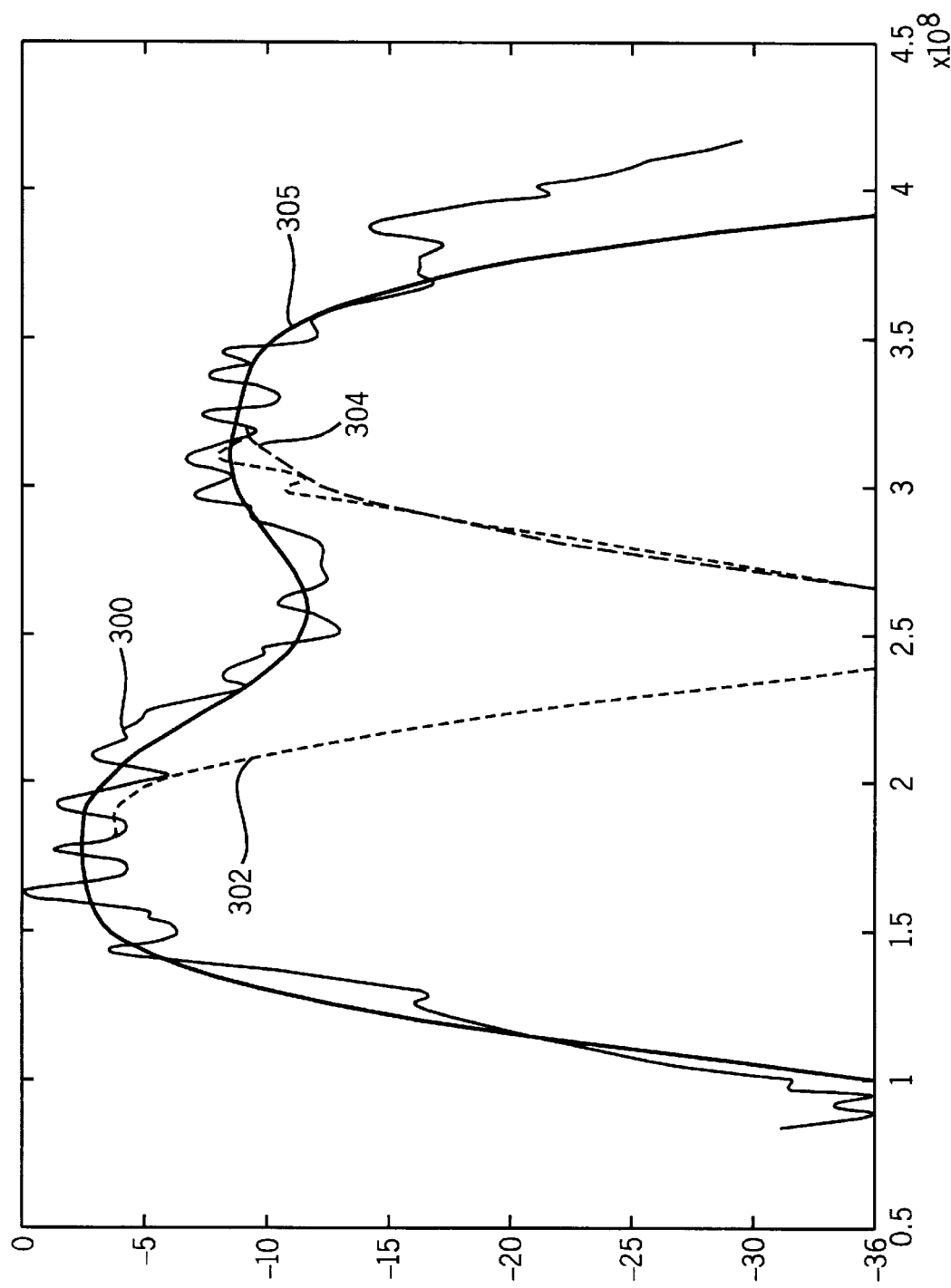
FIG. 6 is a graph illustrating the process steps of the present invention.

Referring now to FIGS. 5 and 6, a flow chart illustrating the process steps taken by the contrast detection processor 122 and corresponding graph illustrating the results are shown. In the initial step 306, the contrast detection processor 122 receives the I and Q values and, then using Fourier methods, calculates a broadband spectrum 300 (FIG. 6) comprising a plurality of data prints plotted in units of decibels versus kilohertz. A broadband spectrum 306 is calculated for the scanned tissue at each point (R,θ) (step 300). From the broadband spectrum 300, in step 310 the contrast detection processor 122 reconstructs a fundamental spectral component 302 which is centered at the ultrasound frequency. To simplify further processing, the fundamental spectral component 302 can be subtracted from the broadband spectrum 300 (step 312), and further processing confined to a reduced set of the spectral data which is not part of the fundamental component 302. From the reduced set of data, in step 314 a harmonic spectral component 304 is reconstructed. The fundamental component 302 and harmonic spectral components 304 can be mathematically reconstructed in steps 310 and 314 using a number of known signal processing techniques including Fourier transforms, cross-correlation functions, or other methods. In the preferred embodiment of the invention, however, the fundamental and harmonic spectral components are reconstructed using a least squares curve fitting method, as described below.

Figure 7:
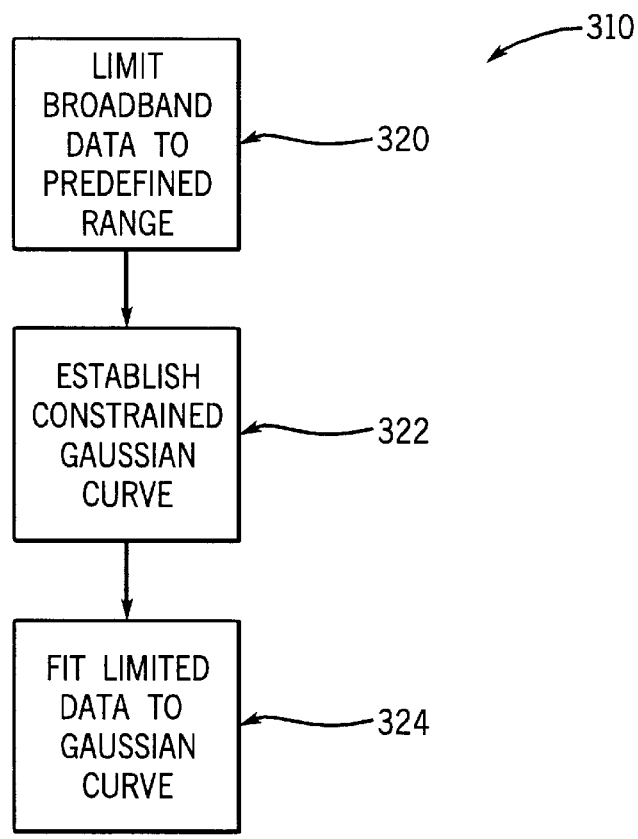
FIG. 7 is a flow chart illustrating the steps for reconstructing the fundamental component in accordance with one embodiment of the invention.

Referring now to FIG. 7, a flow chart illustrating the steps for reconstructing the fundamental spectral component 304 using a least square error fitting process is shown. Since the fundamental spectral component is known to be centered at the ultrasound transmission frequency, in step 320 the broadband spectrum 300 is limited to a predetermined range of data points centered around the ultrasound transmission frequency. By minimizing the data to be examined overlap between the fundamental and harmonic frequencies is minimized. Next, in step 322, limits are placed on the Gaussian curve to constrain the shape of the resultant fundamental spectral component 302. Here, the Gaussian curve is constrained to have a center frequency equivalent to the ultrasound transmission frequency, and to have a predefined standard deviation, where the predefined standard deviation can be established empirically or pre-selected depending on expected output values. After limits are established in steps 320 and 322, in step 324 a least square and fitting method is applied to fit each data point in the limited broadband frequency spectrum to the constrained Gaussian curve.

Figure 8:
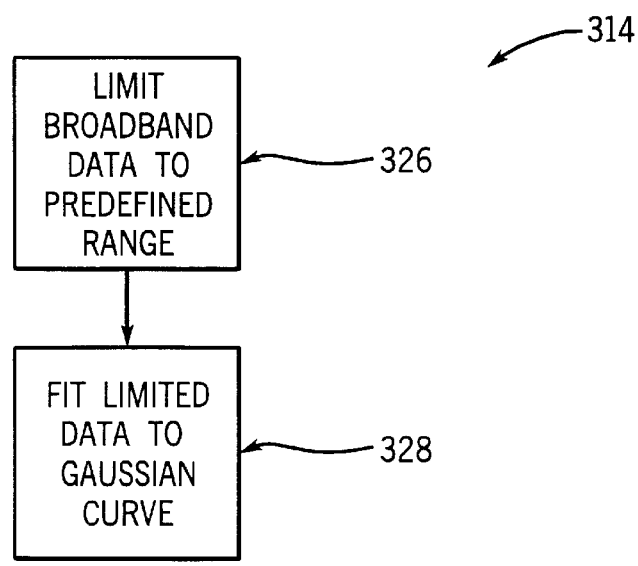
FIG. 8 is a flow chart illustrating the steps for reconstructing the harmonic component in accordance with one embodiment of the invention.

As described above with respect to step 312 (FIG. 5), after the Gaussian curve for the fundamental component is established, the Gaussian curve data is algebraically subtracted from the broadband spectrum 300, such that the remaining limited broadband spectrum includes data points assumed to be associated with the harmonic component. From this limited or reduced spectrum, the harmonic component 304 is reconstructed. Referring now to FIG. 8, the reduced spectrum resulting from the subtraction of the fundamental component is limited to data points in a predefined range, where the range is selected to prevent overlap with both the fundamental component and higher order harmonics, and to prevent a fit beyond the effective range of the transducer filter. In step 328, the remaining data points are again processed using a least squares curve fitting method in which the data is fitted to a Gaussian curve. In reconstructing the harmonic spectral component 304, however, the Gaussian curve is not constrained to a predetermined frequency and standard deviation, since attenuation in the reflected signal can cause the frequency to shift. Using this method, accurate results can be obtained even when the signal is attenuated, as is typically the case in clinical situations.

Referring again to FIG. 5, after the fundamental and harmonic components 302 and 304, respectively, are reconstructed, in step 316 the contrast detection processor 122 examines the data and determines a peak amplitude and a center frequency for each of the fundamental and harmonic components, and uses this data to characterize the tissue at each coordinate (R,θ). Characterization can be provided by calculating the harmonic to fundamental ratio parameter (HFR$_p$), a mathematical comparison of the peak amplitudes of the fundamental and the harmonic components. The resultant HFR$_p$ parameter is used to determine the relative presence of contrast agent in the tissue. Since, as noted above, the presence of the microbubbles introduced by the contrast agent cause significant harmonic components, tissue samples in which the harmonic components are relatively large as compared to the fundamental component can be characterized as having a higher level of contrast agent than those in which the harmonic components are relatively small as compared to the fundamental component.

For quantifying myocardial perfusion, step 316 preferably comprises calculating a difference D between the peak amplitude of the fundamental component 309 and the harmonic component 302. It has been experimentally determined that a range of difference values can be established to characterize perfused versus non-perfused myocardial tissue. If the difference D between the peak amplitude of the fundamental component and the peak amplitude of the harmonic component is greater than 25 dB, there is little or no reflection in the tissue from microbubbles associated with the contrast agent, and the tissue is not perfused. Alternatively, if the difference between the peak amplitude of the fundamental component and the peak amplitude of the harmonic component is greater than 15 dB but less than 25 dB, microbubbles associated with the contrast agent are present in the tissue, and the tissue is therefore perfused. Finally, if the difference between the peak amplitude of the fundamental component and the peak amplitude of the harmonic component is less than 15 dB, microbubbles associated with the contrast agent are present and the tissue is located in the left ventricular cavity (LVC). Similar mathematical comparisons can be drawn using parameters such as a ratio of the peak fundamental amplitude to the peak harmonic amplitude. These comparisons can also be used to characterize the tissue, and to evaluate perfused versus non-perfused tissue.

Referring again to FIG. 6, in some applications it may also be desirable to synthesize or reconstruct the Fourier broadband spectrum 305. The spectrum 305 can be synthesized by applying a curve fitting procedure to fit the curve between the fundamental component 312 and harmonic component 304.

In a preferred embodiment, the method and apparatus of the present invention was tested on a GE Vingmed FiVe ultrasound scanner operating with a 1.7 MHz transmit and 3.4 MHz receive frequency. The scanner was programmed to provide a Fourier broadband spectrum 300 as described above, which could then be analyzed using a least squares curve fitting method also as described above. Here, to reconstruct the fundamental component 302, the broadband data 300 was limited to a range between 1.3 and 2.1 MHz, and the constrained Gaussian curve was centered at 1.7 MHz, with a standard deviation of 0.7 MHz. To reconstruct the harmonic component 304, the frequency range of the broadband spectrum 300 was restricted to the range between 2.3 and 3.7 MHz.

In addition to the contrast detection processor 122, the mid-processor 102 can also provide other imaging calculations. To produce a conventional magnitude image, for example, a detection process indicated at 120 is implemented in which a digital magnitude M is calculated from each beam sample and output at 121.

$$M = (I^2 + Q^2)^{1/2}$$

The detection process 120 may also implement correction methods such as that disclosed in U.S. Pat. No. 4,835,689, issued May 30, 1989 and entitled "Adaptive Coherent Energy Beam Formation Using Phase Conjugation". Such correction methods examine the received beam samples and calculate corrective values that can be used in subsequent measurements by the transmitter 13 and receiver 14 to improve beam focusing and steering. Such corrections are necessary, for example, to account for the non-homogeneity of the media through which the sound from each transducer element travels during a scan.

Figure 4:
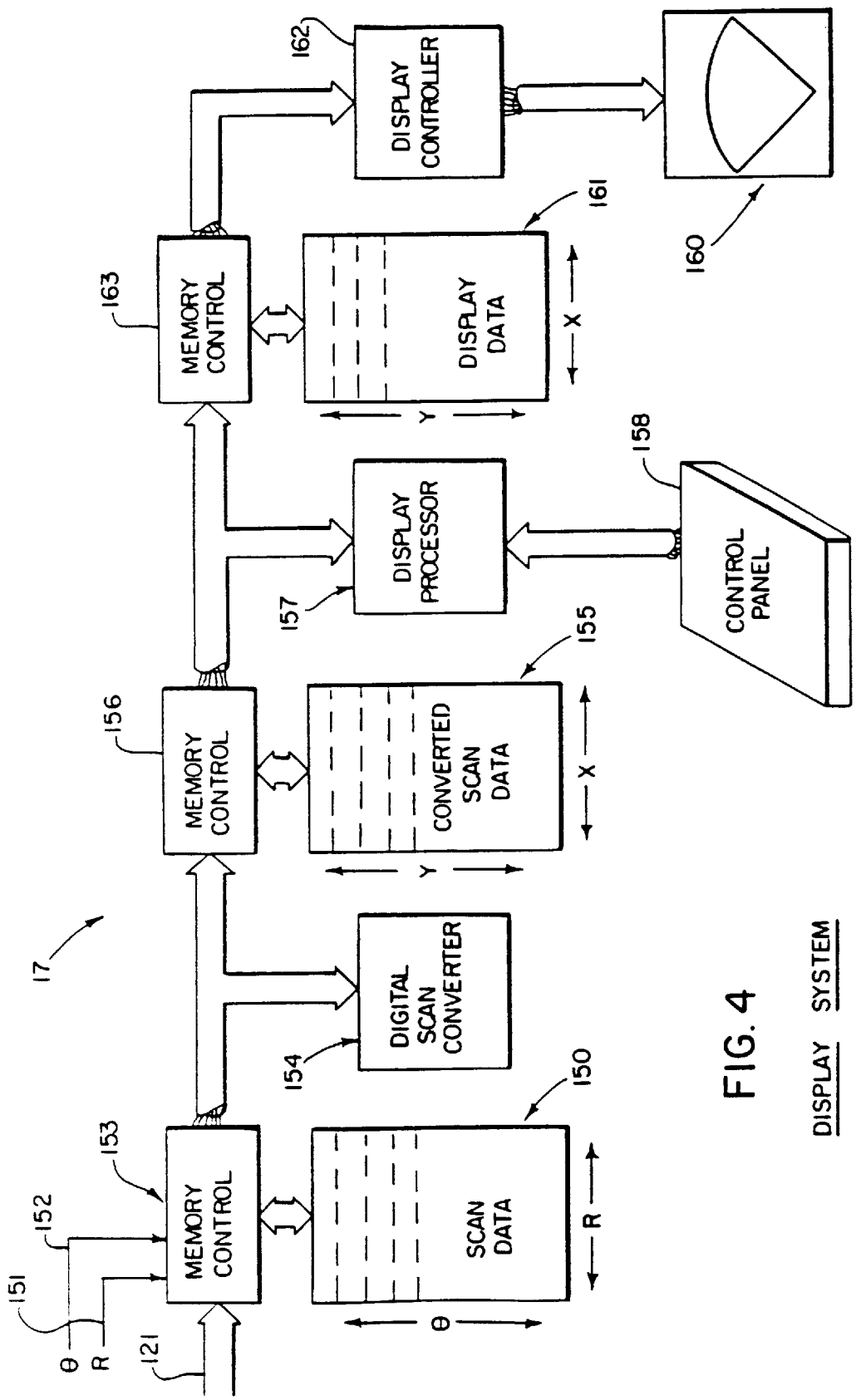
FIG. 4 is a block diagram of a display system which forms part of the system of FIG. 1.

Referring particularly to FIGS. 1 and 4, the receiver 14 generates a stream of 8-bit digital numbers at its output 121 which is applied to the input of the display system 17. This "scan data" is stored in a memory 150 as an array, with the rows of the scan data array 150 corresponding with the respective beam angles ($\theta$) that are acquired, and the columns of the scan data array 150 corresponding with the respective ranges (R) at which samples are acquired along each beam. The R and $\theta$ control signals 151 and 152 from the receiver 14 indicate where each input value is to be stored in the array 150, and a memory control circuit 153 writes that value to the proper memory location in the array 150. The scan can be continuously repeated and the flow of values from the receiver 14 will continuously update the scan data array 150.

Referring still to FIG. 4, the scan data in the array 150 are read by a digital scan converter 154 and converted to a form producing the desired image. In accordance with the present invention the scan data array 150 can store a value characterizing the relative level of contrast agent in the tissue at each set of coordinates (R, $\theta$). This value can be, for example, a ratio such as the HFR$_p$ described above or the difference value D between the peak magnitude of the fundamental component and the harmonic component, also described above. Alternatively, the stored value can be a digital value indicating whether the tissue at each of the defined set of coordinates is perfused myocardial, non-perfused myocardial or perfused LVC myocardial. The values can be converted from polar to Cartesian coordinates to map the image onto pixel locations (x,y) for display. If a conventional B-scan image is also being produced, for example, the magnitude values M(R,$\theta$) stored in the scan data array 150 are converted to magnitude values M(x,y) which indicate magnitudes at pixel locations (x,y) in the image. Such a polar coordinate to Cartesian coordinate conversion of the ultrasonic image data is described, for example, in an article by Steven C. Leavitt et al in Hewlett-Packard Journal, October, 1983, pp. 30–33, entitled "A Scan Conversion Algorithm for Displaying Ultrasound Images". Magnitude images can be used in conjunction with tissue characterization data to provide a detailed output image.

Regardless of the particular conversion made by the digital scan converter 154, the resulting image data are written to a memory 155 which stores a two-dimensional array of converted scan data. A memory control 156 provides dual port access to the memory 155 such that the digital scan converter 154 can continuously update the values therein with fresh data while a display processor 157 reads the updated data. The display processor 157 is responsive to operator commands received from a control panel 158 to perform conventional image processing functions on the converted scan data 155. For example, the range of brightness levels indicated by the converted scan data 155 may far exceed the brightness range of the display device 160. Indeed, the brightness resolution of the converted scan data 155 may far exceed the brightness resolution of the human eye, and manually operable controls are typically provided which enable the operator to select a window of brightness values over which maximum image contrast is to be achieved. The display processor reads the converted scan data from the memory 155, provides the desired image enhancement, and writes the enhanced brightness values to a display memory 161.

The display memory 161 is shared with a display controller circuit 162 through a memory control circuit 163, and the brightness values therein are mapped to control the brightness of the corresponding pixels in the display 160. The display controller 162 is a commercially available integrated circuit which is designed to operate the particular type of display 160 used. For example, the display 160 may be a CRT, in which case the display controller 162 is a CRT controller chip which provides the required sync pulses for the horizontal and vertical sweep circuits and maps the display data to the CRT at the appropriate time during the sweep.

It should be apparent to those skilled in the art that the display system 17 may take many forms depending on the capability and flexibility of the particular ultrasound system. In the preferred embodiment described above, programmed microprocessors are employed to implement the digital scan converter and display processor functions, and the resulting display system is, therefore, very flexible and powerful.

Although preferred embodiments have been shown and described, it will be apparent to one of ordinary skill in the art that a number of modifications could be made to the method and apparatus described without departing from the scope of the invention. It should be understood, therefore, that the methods and apparatuses described above are only illustrative and do not limit the scope of the invention, and that various modifications could be made by those skilled in the art that would fall under the scope of the invention. To apprise the public of the scope of this invention, the following claims are made:

We claim:

1. A method for detecting a contrast agent in the tissue of a subject using ultrasonic signals, the method comprising the following steps:
   (a) directing an ultrasound pulse signal having a selected transmission frequency at a region of interest in the subject;
   (b) receiving an echo signal from the region of interest;
   (c) generating a Fourier broadband spectrum from the received echo signal;
   (d) mathematically synthesizing a fundamental spectral component centered around the selected transmission frequency using the Fourier broadband spectrum;
   (e) mathematically reconstructing a harmonic spectral component using the Fourier broadband spectrum; and
   (f) determining a relationship between the energy characteristics of the fundamental spectral component and the harmonic spectral component, wherein the relationship indicates a proportion of the echo signal that is returned from contrast agent versus a proportion which is returned from tissue.

2. The method as defined in claim 1, wherein step (d) further comprises:
   i. limiting the Fourier broadband spectrum to a pre-selected frequency range substantially centered around the transmission frequency to provide a limited broadband Fourier spectrum; and
   ii. applying a least squares curve fitting method to the limited broadband Fourier spectrum to produce a Gaussian curve substantially centered at the transmission frequency.

3. The method as defined in claim 2, wherein step (ii) further comprises constraining the Gaussian curve to be centered at the transmission frequency.

4. The method as defined in claim 2, wherein step (ii) further comprises constraining the Gaussian curve to have a standard deviation of 0.7 MHz.

5. The method as defined in claim 1, wherein step (e) further comprises:
   i. limiting the Fourier broadband spectrum to a pre-selected range, the pre-selected range having a minimum frequency substantially equivalent to the maximum expected value of the fundamental harmonic component, and having a maximum frequency less than the expected minimum frequency of the third harmonic to provide a limited broadband Fourier spectrum;
   ii. applying a least squares curve fitting method to the limited broadband Fourier spectrum to produce a Gaussian curve of the harmonic spectral component.

6. The method as defined in claim 5, wherein step (i) further comprises the step of subtracting the fundamental component from the Fourier broadband spectrum.

7. The method as defined in claim 1, wherein step (f) further comprises:
   i. determining a peak amplitude value for each of the fundamental and the harmonic components;
   ii. determining a difference between the peak amplitude of the fundamental component and the peak amplitude of the harmonic component; and
   iii. determining an amount of contrast agent in the tissue based on the difference.

8. The method as defined in claim 7, wherein step iii comprises comparing the difference to a predetermined scale of difference values, the predetermined scale providing a characterization of whether myocardial tissue is perfused or not perfused.

9. The method as defined in claim 8, wherein the tissue is perfused if the difference value is less than twenty-five decibels and the tissue is non-perfused if the difference value is greater than twenty-five decibels.

10. The method as defined in claim 9, wherein tissue having a difference of more than fifteen decibels is characterized as prefused LVC tissue.

11. The method as defined in claim 1, wherein step (f) further comprises:
   i. determining a peak amplitude value for each of the fundamental and the harmonic components;
   ii. determining a ratio between the peak amplitude of the fundamental component and the peak amplitude of the harmonic component; and
   iii. determining an amount of contrast agent in the tissue based on the ratio.

12. An ultrasonic imaging system for detecting a contrast agent in the tissue of a subject, the apparatus comprising:
   (a) an ultrasonic transducer array having a set of array elements disposed in a pattern and each being separately operable to produce a pulse of ultrasonic energy during a transmission mode and each being operable to produce an echo signal in response to ultrasonic energy which impinges on the array element during a receive mode;
   (b) a transmitter connected to the ultrasonic transducer array and being operable during the transmission mode to apply a separate signal to each array element such that a steered transmit beam is produced;
   (c) a receiver connected to the ultrasonic transducer array and being operable during the receive mode to sample the echo signal produced by each array element as the ultrasonic energy impinges thereon and to form a beam signal therefrom by separately delaying and summing the separate echo signals sampled from each transducer element;

(d) a processor connected to the receiver to receive the beam signal, the processor being programmed to:

(i) determine a Fourier broadband spectrum at each of a plurality of sets of coordinates, the coordinates being correlated to an angle and a depth in the tissue;

(ii) reconstruct a fundamental spectral component and a harmonic spectral component for the Fourier broadband spectrum at each set of coordinates; and (iii) calculate a contrast relationship between the energy characteristics of the fundamental spectral component and the harmonic spectral component for each of the plurality of sets of coordinates, wherein the contrast relationship indicates a proportion of the beam signal that is returned from contrast agent versus a proportion which is returned from tissue at each point; and (e) a display system connected to receive the contrast relationship for each set of coordinates and to produce an image therefrom, the image providing a visual indication of the contrast agent in the tissue.

13. The system of claim 12, wherein the processor is further programmed to apply a least squares Gaussian curve fitting process to the Fourier broadband spectrum to reconstruct the fundamental component and the harmonic component.

14. The system of claim 13, wherein the processor is further programmed to constrain the fundamental component to a center frequency substantially equivalent to the transmission frequency of the transmitter.

15. The system as defined in claim 12, wherein the contrast relationship comprises a difference between a peak amplitude of the fundamental spectral component and the harmonic spectral component.

16. The system as defined in claim 12, wherein the contrast relationship comprises a ratio of a peak amplitude of the fundamental component and a peak amplitude of the harmonic component.

17. The system as defined in claim 12, wherein the processor is further programmed to compare the contrast relationship to a predetermined scale, the predetermined scale providing an indication of whether the tissue is perfused or non-perfused.

18. A method for evaluating myocardial perfusion by detecting a contrast agent in the tissue of a subject using ultrasonic signals, the method comprising the following steps:

(a) directing an ultrasound pulse signal having a selected transmission frequency at a region of interest in the subject;

(b) receiving an echo signal from the region of interest;

(c) generating a Fourier broadband spectrum comprising a plurality of data points from the received echo signal;

(d) limiting the Fourier broadband spectrum to a reduced set of data points defined in a frequency range around the selected transmission frequency range;

(e) applying a least squares curve fitting procedure to each data point in the reduced set of data points to fit the reduced set of data points to a Gaussian curve and to mathematically reconstruct a fundamental spectral component centered around the selected transmission frequency from the echo signal, (f) subtracting the fundamental spectral component from the Fourier broadband spectrum to provide a second reduced set of data points;

(g) applying a least squares curve fitting procedure to fit the second reduced set of data points to a Gaussian curve to mathematically reconstruct the harmonic spectral component from the echo signal;

(h) determining a peak amplitude value for each of the fundamental spectral component and the harmonic spectral component;

(i) determining a difference between the peak amplitude of the fundamental spectral component and the peak amplitude of the harmonic spectral component; and (j) comparing the difference to a predetermined scale to determine whether the tissue is perfused or non-perfused.

19. The method as defined in claim 18, wherein if the difference is greater than twenty five decibels the tissue is non-perfused.

20. The method as defined in claim 18, wherein if the difference is less than twenty five decibels the tissue is perfused.

21. The method as defined in claim 18, further comprising the step of comparing the difference to the predetermined scale to determine whether the tissue is from the left ventricular cavity.

* * * * *